US009445191B2

(12) United States Patent
Christoph

(10) Patent No.: US 9,445,191 B2
(45) Date of Patent: Sep. 13, 2016

(54) METHOD OF ADJUSTING AN ACTIVE NOISE CANCELLING SYSTEM

(71) Applicant: HARMAN BECKER AUTOMOTIVE SYSTEMS GMBH, Karlsbad (DE)

(72) Inventor: Markus Christoph, Straubing (DE)

(73) Assignee: Harman Becker Automotive Systems GmbH, Karlsbad (DE)

( * ) Notice: Subject to any disclaimer, the term of this patent is extended or adjusted under 35 U.S.C. 154(b) by 0 days.

(21) Appl. No.: 14/375,519

(22) PCT Filed: Jan. 28, 2013

(86) PCT No.: PCT/EP2013/051558

§ 371 (c)(1),
(2) Date: Jul. 30, 2014

(87) PCT Pub. No.: WO2013/113649

PCT Pub. Date: Aug. 8, 2013

(65) Prior Publication Data

US 2015/0010164 A1 Jan. 8, 2015

(30) Foreign Application Priority Data

Jan. 31, 2012 (EP) .................................... 12153335

(51) Int. Cl.
*A61F 11/06* (2006.01)
*G10K 11/16* (2006.01)
(Continued)

(52) U.S. Cl.
CPC ............ *H04R 3/002* (2013.01); *G10K 11/178* (2013.01); *H04R 1/1083* (2013.01);
(Continued)

(58) Field of Classification Search
CPC ... A61F 11/06; G10K 11/175; G10K 11/178; G10K 2210/1081; G10K 2210/3048; G10K 2210/3055; H04R 1/10; H04R 1/28; H04R 1/1083; H04R 1/1091; H04R 5/033; H04R 25/00; H04R 25/75; H04R 2400/01; H04R 2410/00; H04R 2410/01; H04R 2410/05; H04R 2410/07; H04R 2460/01
USPC ...... 381/41, 42, 43, 46, 71.1, 71.6, 72, 73.1, 381/74, 94.1, 370
See application file for complete search history.

(56) References Cited

U.S. PATENT DOCUMENTS 6,163,610 A * 12/2000 Bartlett .................. H04M 1/03 379/433.01
8,085,943 B2 * 12/2011 Bizjak ................. H03G 3/3089 381/107

(Continued)

FOREIGN PATENT DOCUMENTS

CN 101577847 A 11/2009
CN 102280102 A 12/2011

(Continued)

OTHER PUBLICATIONS

Nelson, et al., "Active Control of Sound," Academic Press (1992), (244 pages).

(Continued)

*Primary Examiner* — Khai N Nguyen
(74) *Attorney, Agent, or Firm* — Brooks Kushman P.C.

(57) ABSTRACT

A method of adjusting an ANC system is disclosed in which a microphone is acoustically coupled to a loudspeaker via a secondary path and the loudspeaker is electrically coupled to the microphone via an ANC filter. The method includes measuring phase characteristics of the secondary path in various modes of operation; determining from the measured phase characteristics a statistical dispersion of the phase characteristics in the various modes of operation; determining from the statistical dispersion a minimum phase margin; adjusting the ANC filter to exhibit in any one of the modes of operation phase characteristics that are equal to or greater than the minimum phase margin; and adjusting the ANC filter to exhibit in any one of the modes of operation amplitude characteristics that are equal to or smaller than a maximum gain margin.

12 Claims, 4 Drawing Sheets

(51) Int. Cl.

| | |
|---|---|
| ***H03B 29/00*** | (2006.01) |
| ***H04B 15/00*** | (2006.01) |
| ***H04R 3/00*** | (2006.01) |
| ***H04R 1/10*** | (2006.01) |
| ***G10K 11/178*** | (2006.01) |

(52) U.S. Cl.
CPC ................ *G10K 2210/1081* (2013.01); *G10K 2210/3048* (2013.01); *G10K 2210/3055* (2013.01); *H04R 2410/05* (2013.01); *H04R 2430/01* (2013.01)

(56) References Cited

U.S. PATENT DOCUMENTS

| | | | | |
|---|---|---|---|---|
| 2003/0079937 A1 | 5/2003 | Vaishaya | | |
| 2008/0112570 A1* | 5/2008 | Asada | G10K 11/1782 | 381/71.6 |
| 2009/0279709 A1* | 11/2009 | Asada | G10K 11/178 | 381/71.1 |
| 2010/0215190 A1* | 8/2010 | Itou | G10K 11/1786 | 381/94.2 |

FOREIGN PATENT DOCUMENTS

| | | | |
|---|---|---|---|
| EP | 1577879 A1 | 9/2005 | |
| EP | 1947642 A1 | 7/2008 | |
| JP | 2007240704 A | 9/2007 | |

OTHER PUBLICATIONS

Elliott, "Signal Processing for Active Control," Acadmeic Press (2001), (266 pages).

Adachi, et al., "Modeling, Control and Experiment of a Feedback Active Noise Control System for Free Sound Fields," (Jun. 4, 2003), (22 pages).

Elliott, "A Review of Active Noise and Vibration Control in Road Vehicles," ISVR, University of Southampton, (Dec. 2008), (26 pages).

Hansen, et al., "Active Control of Noise and Vibration," Dept. of Mechanical Engineering, Univeristy of Adelaide, South Australia, E & FN Spon, (1997), (20 pages).

Kataja, et al., "An Optimisation-Based Design Method for Analogue Feedback Controllers for Active Noise Control," ISVR, Southampton, UK, (Jul. 15-17, 2002), (8 pages).

Kataja, et al., "Optimisation of digitally adjustable analogue biquad filters in feedback active control," ForumAcusticum, (2005), (4 pages).

Nelder, et al., "A simplex method for function minimization," Computer Journal, (6 pages).

Veloso, et al., "Headhphone with Active Noise Control using Analog Adaptive Filers," RIO 2005 Inter-noise, Environmental Noise Control, (Aug. 7-10, 2005), (8 pages).

EP Search dated Sep. 10, 2012 for EP121533350.0 (5 pages).

PCT International Search Report & Opinion dated Feb. 27, 2013 for PCT/EP2013/051558 (8 pages).

Elliot, "Signal Processing for Active Control," Acadmeic Press (2001), (266 pages).

Chinese Patent Office, Office Action dated Dec. 4, 2015 for CN2015120100027950.

Wang, "Simulation of Adaptive Active Noise Control System," College of Hydroelectricity and Digitalization, China, 2004, (3 pages).

* cited by examiner

| | $f_1$ | $f_2$ | $f_3$ | .. | $f_q$ |
|---|---|---|---|---|---|
| User 1 | $\varphi_{11}$ | $\varphi_{12}$ | $\varphi_{13}$ | .. | $\varphi_{1q}$ |
| User 2 | $\varphi_{21}$ | $\varphi_{22}$ | $\varphi_{23}$ | .. | $\varphi_{2q}$ |
| User 3 | $\varphi_{31}$ | $\varphi_{323}$ | $\varphi_{33}$ | .. | $\varphi_{3q}$ |
| User 4 | $\varphi_{41}$ | $\varphi_{42}$ | $\varphi_{43}$ | .. | $\varphi_{4q}$ |
| User 5 | $\varphi_{51}$ | $\varphi_{52}$ | $\varphi_{53}$ | .. | $\varphi_{5q}$ |
| : | : | : | : | :. | $\varphi_{6q}$ |
| User p | $\varphi_{p1}$ | $\varphi_{p2}$ | $\varphi_{p3}$ | .. | $\varphi_{pq}$ |

METHOD OF ADJUSTING AN ACTIVE NOISE CANCELLING SYSTEM

CROSS-REFERENCE TO RELATED APPLICATION

This application is the U.S. national phase of PCT Application No. PCT/EP2013/051558filed on Jan. 28, 2013, which claims priority to EP Patent Application No. 12 153 335.0filed on Jan. 31, 2012, the disclosures of which are incorporated in their entirety by reference herein.

BACKGROUND

The invention relates to a method of adjusting an ANC system and, in particular, to a method of adjusting an ANC system for maximum noise attenuation.

In feedback automatic noise control (ANC) systems, a microphone is acoustically coupled to a loudspeaker via a secondary path and the loudspeaker is electrically coupled to the microphone via an ANC filter. Feedback ANC systems are particularly used in arrangements in which the microphone needs to be arranged relatively close to the loudspeaker as, for instance, in ANC headphones. Regardless of the particular application, feedback ANC systems are commonly adjusted according to a (weighted) sensitivity function which is the transfer function of a signal path between a noise source that generates a disturbing signal d[n] and the microphone that receives an error signal e[n]. A transfer function is a mathematical representation, in terms of (temporal) frequency, of the relation between the input (e.g., the disturbing signal d[n]) and the output (e.g., the error signal e[n]) of an essentially time-invariant system (e.g., the primary path of an ANC system).

Feedback ANC systems are often implemented in analog circuitry and/or as non-adaptive, i.e., fixed filters so that subsequent adaption to different modes of operation is difficult or even impossible. For instance in headphones, different users wearing the headphones create different secondary paths and, thus, different modes of operation. Careful adjustment of the filters at the time of the filter design is, therefore, vital for a satisfactory performance of the ANC system that is to be operated in different modes of operation. Satisfactory performance means, e.g., providing a stable control loop with a high noise attenuation in a large frequency band. Commonly, minimizing the (weighted) sensitivity function N(z) is employed to provide higher attenuations. However, the performance achieved in this way is often considered to be insufficient.

United States Patent Application Publication 2010/0215190A1 discloses a method of adjusting an ANC system in which a microphone is acoustically coupled to a loudspeaker via a secondary path and the loudspeaker is electrically coupled to the microphone via an ANC filter.

There is a need to provide an improved method of adjusting an ANC system for maximum noise attenuation.

SUMMARY

A method of adjusting an ANC system is disclosed in which a microphone is acoustically coupled to a loudspeaker via a secondary path and the loudspeaker is electrically coupled to the microphone via an ANC filter. The method comprises measuring phase characteristics of the secondary path in various modes of operation; determining from the measured phase characteristics a statistical dispersion of the phase characteristics in the various modes of operation; determining from the statistical dispersion a minimum phase margin; adjusting the ANC filter to exhibit in any one of the modes of operation phase characteristics that are equal to or greater than the minimum phase margin; and adjusting the ANC filter to exhibit in any one of the modes of operation amplitude characteristics that are equal to or smaller than a maximum gain margin.

BRIEF DESCRIPTION OF THE DRAWINGS

Various specific embodiments are described in more detail below based on the exemplary embodiments shown in the figures of the drawing. Unless stated otherwise, similar or identical components are labeled in all of the figures with the same reference numbers.

DETAILED DESCRIPTION

Figure 1:
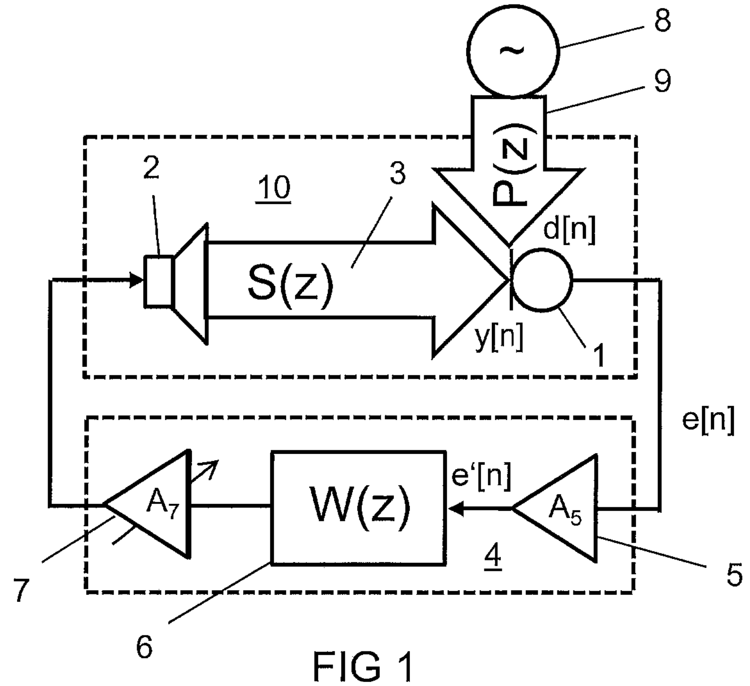
FIG. 1 is a block diagram illustrating the principles of signal processing in a feedback ANC system.

Reference is now made to FIG. 1, which is a block diagram illustrating the principles of signal processing in a feedback ANC system. In the ANC system of FIG. 1, an error microphone 1 is acoustically coupled to a loudspeaker 2 via a secondary path 3 and the loudspeaker 2 is electrically coupled to the microphone 1 via a feedback signal path 4 including a microphone pre-amplifier 5, a subsequent ANC filter 6 with a transfer function W(z) and a subsequent loudspeaker driver amplifier 7 whose amplification $A_7$ is adjustable or controllable. The microphone 1 and the loudspeaker 2 may be arranged in a room 10, e.g., the room enclosed by an earphone and a user's head. The term "loudspeaker" as used herein means any type of transducer that converts electrical signals it receives into acoustic signals that it radiates. Accordingly, the term "microphone" as used herein means any type of transducer that converts acoustic signals it receives into electrical signals that it provides.

The microphone 1 receives an acoustic signal that is composed of an acoustic output signal y(t) and an acoustic disturbance signal d(t). Output signal y(t) is the output signal of the loudspeaker 2 filtered with a transfer function S(z) of the secondary path 3 and disturbance signal d(t) is the output signal of a noise source 8 filtered with a transfer function P(z) of a primary path 9. From this received acoustic signal y(t)-d(t), the microphone 1 generates an electrical error signal e(t) which is amplified by the microphone pre-amplifier 5 and then supplied as amplified error signal e(t)=$A_5$ e(t) to the subsequent ANC filter 6. For the sake of simplicity, the amplification $A_5$ of microphone pre-amplifier 5 is assumed to be equal to 1 in the considerations below so that e(t)=e(t), but may have any other appropriate value as required.

The ANC system shown in FIG. 1 can be described by the following differential equations in the spectral domain based on the various signals in the time domain, in which D(z), E(z) and Y(z) are the spectral representations of the signals d(t), e(t) and y(t) in the time domain.

$$E(z)=D(z)-Y(z),$$

$$Y(z)=E(z)\cdot W(z)\cdot S(z).$$

Thus, the sensitivity function N(z), which is the disturbance signal to error signal ratio, can be described as:

$$N(z)=D(z)/E(z)=1/(1+W(z)\cdot S(z))=1/(1+H_{OL}(z)),$$

in which $H_{OL}(z)=W(z)\cdot S(z)$ is the transfer function of the open loop of the feedback ANC system.

The differentiation equation of a complementary sensitivity function T(z), which is the disturbance signal d(t) to output signal y(t) ratio, is accordingly:

$$T(z)=D(z)/Y(z)=H_{OL}(z)/(1+H_{OL}(z)).$$

When calculating the robust stability of a feedback ANC system, commonly a so-called $H_\infty$ or $H_2$ norm or a combination of both ($H_\infty/H_2$) is used. In the $H_\infty$ norm, the open loop is optimized with regard to the maximum of the absolute value of the complementary sensitivity function T(z) so that, taking into account an uncertainty bound B(z) that addresses fluctuations in the secondary path 3, the norm $H_\infty$ does not exceed 1.

$$\max(|T(z)\cdot B(z)|)=\|T(z)\cdot B(z)\|_\infty<1.$$

In the $H_2$ norm, the following condition is to be complied with:

$$\left((1/2\pi)\int_{-\infty}^{\infty}(|T(z)|\cdot B(z)|^2|X(z)|d\omega\right)^{-1/2}=\|T(z)\cdot B(z)\|_2\|X(z)\|_2<1.$$

As can be seen from the two equations above, the $H_\infty$ norm relates to the worst case possible of the $H_2$ norm as it is independent of the underlying disturbing signal in contrast to the $H_2$ norm which considers the characteristics of a potential disturbing signal and which represents the average amplification of the ANC system.

Figure 2:
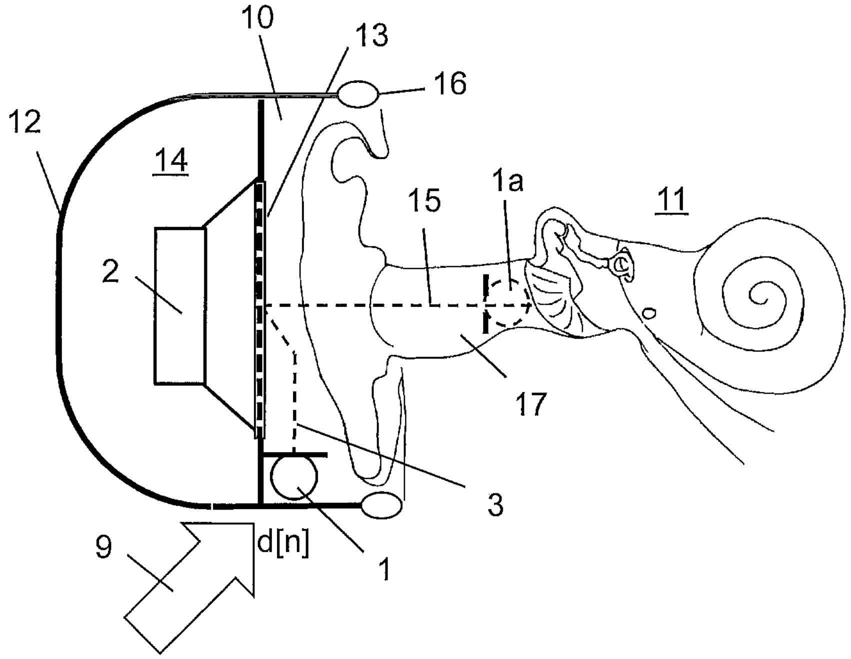
FIG. 2 is a schematic diagram of an earphone to which the active noise reduction system shown in FIG. 1 may be applied.

FIG. 2 illustrates an exemplary earphone with which the active noise reduction systems shown in FIG. 1 may be used. The earphone may be, together with another identical earphone, part of a headphone (not shown) and may be acoustically coupled to a listener's ear 11. In the present example, the ear 11 is exposed via primary path 9 to the disturbing signal d[n], e.g., ambient noise. The earphone comprises a cup-like housing 12 with an aperture 13 that may be covered by a sound permeable cover, e.g., a grill, a grid or any other sound permeable structure or material.

The loudspeaker 2 radiates sound to the ear 11 and is arranged at the aperture 13 of the housing 12, both forming an earphone cavity 14. The cavity 14 may be airtight or vented by any means, e.g., by means of a port, vent, opening, etc. The microphone 1 is positioned in front of the loudspeaker 2. An acoustic path 15 extends from the loudspeaker 2 to the ear 11 and has a transfer characteristic which is approximated for noise control purposes by the transfer characteristic of the secondary path 3 which extends from the loudspeaker 2 to the microphone 1. In the present exemplary earphone, the room 10 is enclosed by the housing 12, the front side of loudspeaker 2, a head rest 16 and the user's ear 11 including ear canal 17.

Figure 3:
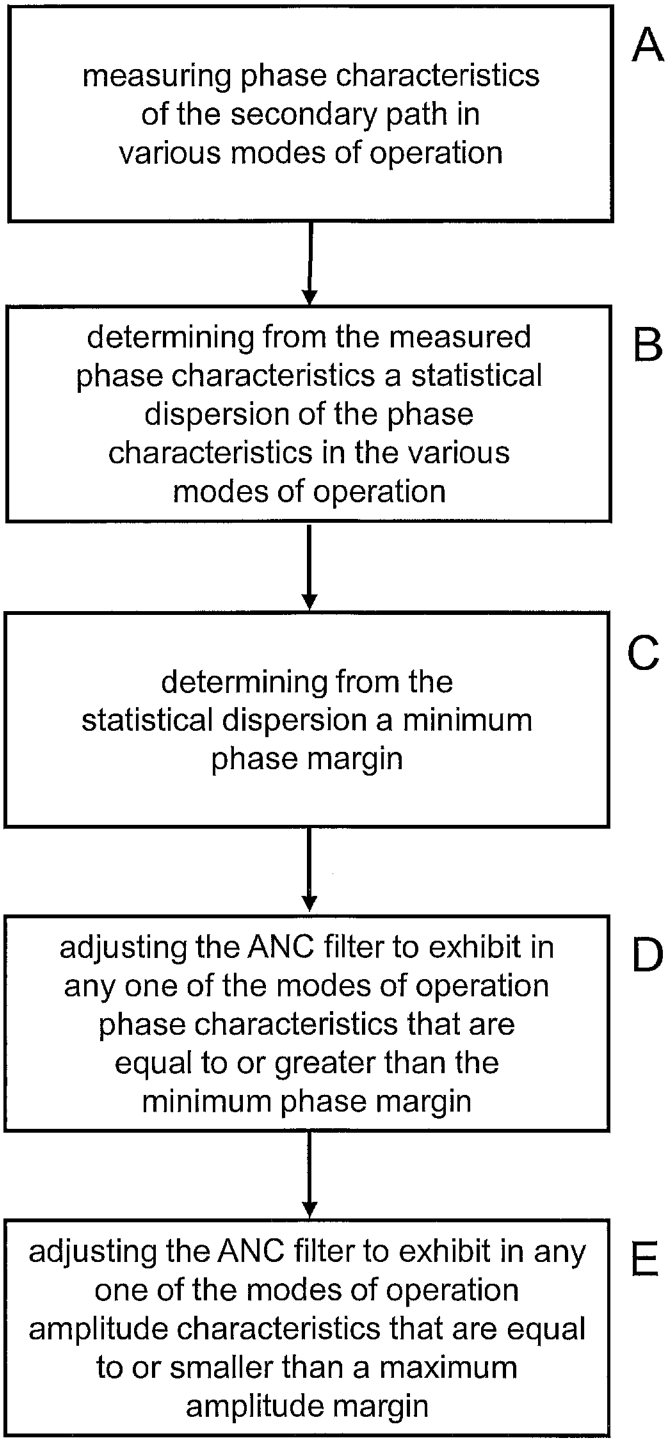
FIG. 3 is a flow diagram illustrating an improved method of adjusting an ANC system.

FIG. 3 is a flow diagram illustrating an improved method of adjusting a (feedback) ANC system (e.g., the system of FIG. 1) in which a microphone (e.g., microphone 1) is acoustically coupled to a loudspeaker (e.g., loudspeaker 2) via a secondary path (e.g., secondary path 3) and the loudspeaker is electrically coupled to the microphone via an ANC filter (e.g., ANC filter 6).

Figures 4, 5:
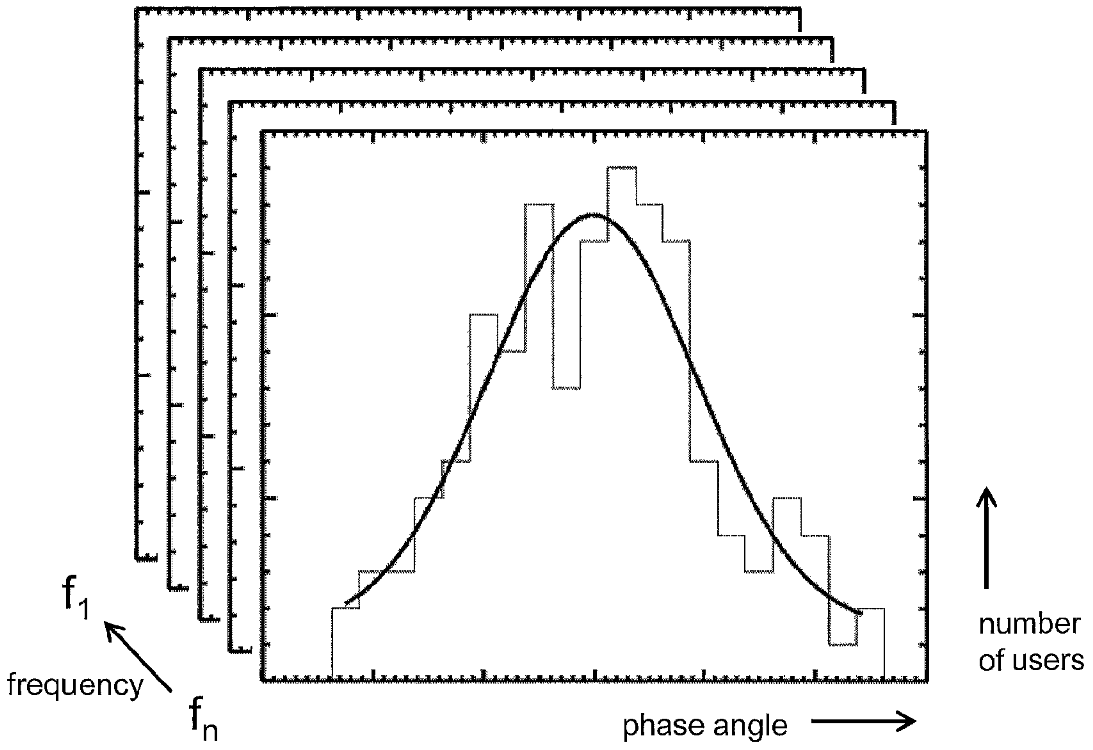
FIG. 4 is an exemplary table linking phase angles to different users and different frequencies.
FIG. 5 is a diagram illustrating an exemplary statistical dispersion of the measurements as set forth in the table of FIG. 4.

In the improved method, the phase characteristics of the secondary path (3) are measured in various modes of operation (step A in FIG. 3). For instance in headphones, different modes of operation may be established by different users wearing the headphones users wearing the headphone in different ways thereby creating different secondary paths. In vehicle cabins, different occupants or a different number of occupants may create different secondary paths. For a multiplicity of different modes of operation (e.g., for different users) at least one measurement is performed and statistically evaluated in view of the phase characteristics, i.e., phase over frequency. In FIG. 4 an exemplary table linking phase angles that have been measured for different users, namely users 1 . . . p, and different frequencies $f_1 \ldots f_q$ is shown. The values in the table have been determined by measuring the phase angles of the secondary path for each of the users 1 . . . p at each of the frequencies $f_1 \ldots f_q$. If more than one measurement is made per user and frequency, the mean average or any other type of average may be employed as a single value per user and frequency.

From the measured phase characteristics (phase vs. frequency) a statistical dispersion of the phase characteristics in the various modes of operation is determined (step B in FIG. 3). Statistical dispersion, also known as statistical variability or variation, is the variability or spread in a variable or a probability distribution. Common examples of measures of statistical dispersion are the variance, standard deviation and interquartile range. In the present case, such variability results from measurements (including measurement errors) in different modes of operation. An exemplary statistical dispersion of the measured phase angles ($\phi_{11} \ldots \phi_{pq}$ as set forth in the table of FIG. 4 is shown in FIG. 5 in which for each frequency $f_1 \ldots f_q$ a dispersion of the number of users per phase angle is furnished.

From the statistical dispersion the minimum phase margin is determined (step C in FIG. 3). This may be achieved by creating for each of secondary paths (secondary path per mode of operation) a Bode diagram and by subsequently determining the worst case magnitude characteristic (magnitude over frequency) and/or the phase characteristic (phase over frequency), e.g., by furnishing a phase characteristic that includes those phase values which are closest to the stability limits at 0° and 360° at each of a multiplicity of frequencies.

From the dispersion at the lower stability limit at 360° the phase margins are determined, e.g., by multiplying each spread of distribution with a constant. The gain margins may be determined on the basis of the (frequency dependent) spread of distribution of the magnitude characteristic at each of the multiple frequencies. However, this value may also be used for estimating how much the gain can be reduced with a given filter design in order to achieve a higher stability or robustness of the filter and in which the gain margin is as small as possible, e.g., equal to or smaller than 1 dB or 0.5 dB or 0.25 dB.

In order to improve the accuracy of the measurements the microphone 1 may be arranged in the ear canal 17 as shown in FIG. 2 (denoted as 1'). Furthermore, the amplitude margin or the phase margin or both may be frequency-independent.

An asymptotically stable feedback system may become marginally stable if the loop transfer function changes. The gain margin GM (also known as amplitude margin) and the phase margin PM (radians or degrees $\phi$) are stability margins which in their own ways expresses the size of parameter changes that can be tolerated before an asymptotically stable system becomes marginally stable.

Figure 6:
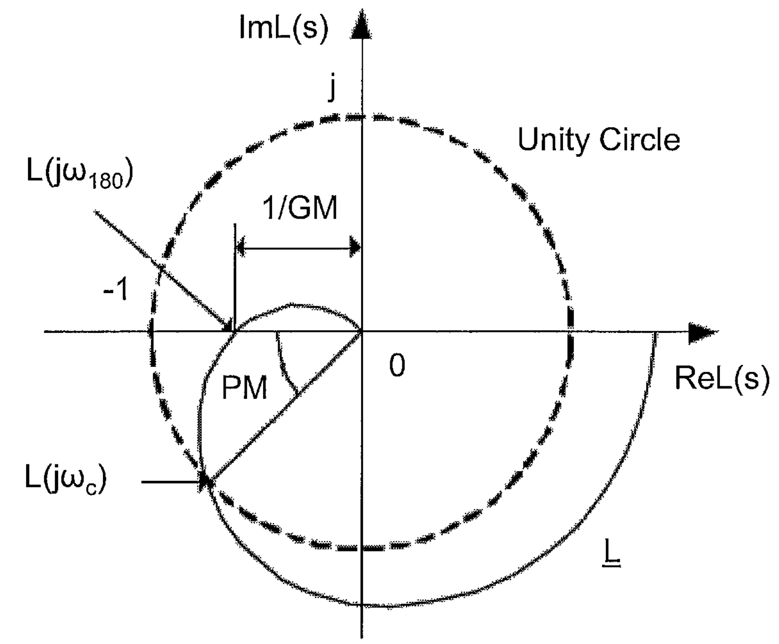
FIG. 6 is a Nyquist diagram in which the stability margins are defined.

FIG. 6 shows the stability margins defined in a Nyquist diagram. GM is the (multiplicative, not additive) increase of the gain that L can tolerate at $\omega_{180}$ before the L curve (in the Nyquist diagram) passes through the critical point $\omega_c$. Thus, $$|L(j\omega_{180})|\cdot GM=1$$

which gives $$GM=1/|L(j\omega_{180})|=1/|ReL(j\omega_{180})|$$

The latter expression is thus given because at $\omega_{180}$, the imaginary part ImL(s)=0 so that the amplitude is equal to the absolute value of the real part ReL(s).

If using decibel as the unit like in a Bode diagram, then $$GM\ [dB]=-|L(j\omega_{180})|[dB]$$

The phase margin PM is the phase reduction that the L curve can tolerate at $\omega_c$ before the L curve passes through the critical point. Thus, $$\arg L(j\omega_c)-PM=-180°$$

which gives $$PM=180°+\arg L(j\omega c).$$

Accordingly, the feedback (closed) system is asymptotically stable if $$GM>0dB=1 \text{ and } PM>0°.$$

This criterion is often denoted the Bode-Nyquist stability criterion. Thus, the closed loop system is marginally stable if the Nyquist curve (of L) goes through the critical point, which is the point (−1, 0) in the Nyquist diagram.

Figure 7:
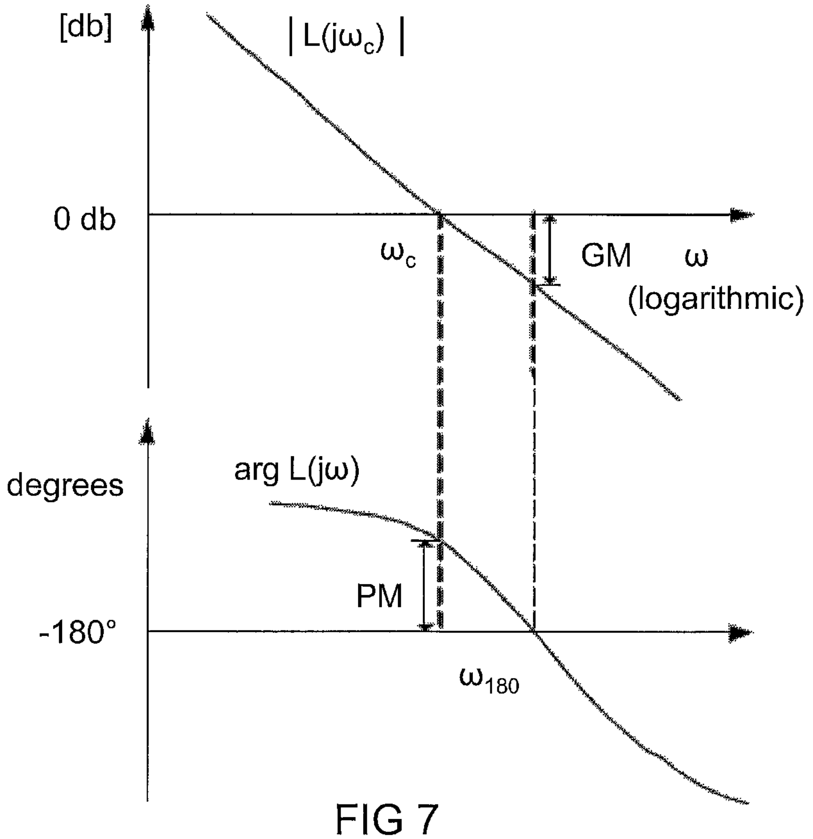
FIG. 7 is a Bode diagram in which the stability margins are defined.

In a Bode diagram, the critical point has phase (angle) −180° and amplitude 1=0 dB. The critical point therefore constitutes two lines in a Bode diagram: The 0 dB line in the amplitude diagram and the −180° line in the phase diagram. FIG. 7 shows typical L curves for an asymptotically stable closed loop system.

Commonly used ranges of the stability margins are $$2\approx 6\ dB\leq GM\leq 4\approx 12\ dB \text{ and } 30°\leq PM\leq 60°.$$

The larger values, the better stability, but at the same time the system becomes more sluggish, dynamically. If the stability margins are used as design criterias, the following values commonly apply:

$$GM\geq 2.5\approx 8\ dB \text{ and } PM\geq 45°$$

However, the present ANC filter 6 is adjusted (designed) such that it exhibits in any one of the modes of operation phase characteristics that are equal to or greater than the minimum phase margin PM determined in step C (step D in FIG. 3), which may be 40° or 30° or even below 30°.

The ANC filter 6 is also adjusted (designed) to exhibit in any one of the modes of operation amplitude characteristics that are equal to or smaller than a maximum amplitude margin (step E in FIG. 3).

Per definition the stability margins express the robustness of the feedback control system against certain parameter changes in the loop transfer function. The gain margin GM is how much the loop gain K can increase before the system becomes unstable. The phase margin PM is how much the phase lag function of the loop can be reduced before the loop becomes unstable.

The gain margin GM may be determined, in a similar manner as the phase margin PM, from the statistical dispersion. Alternatively, the gain margin GM may be kept as small as possible so that the system is close to marginal stability or even instability. Also a (small) fixed maximum gain margin GM, e.g., GM <1dB or 0.5dB or even 0.25dB, may be used. The desired robustness is then achieved by reducing the loop gain K by a value that is determined from the statistical dispersion.

Adjusting (designing) of the ANC filter is accomplished by accordingly designing or adjusting the transfer function W(z) of the ANC filter 6 so that all the requirements outlined above are met. It is to be noted that the order of the steps (A to E) and the steps per se may be changed. Also the number of steps may be increased or decreased as the case may be. Although various examples of realizing the invention have been disclosed, it will be apparent to those skilled in the art that various changes and modifications can be made which will achieve some of the advantages of the invention without departing from the spirit and scope of the invention. It will be obvious to those reasonably skilled in the art that other steps and measures performing the same functions may be suitably substituted. In particular, the order of the steps and the steps per se may be changed. Such modifications to the inventive concept are intended to be covered by the appended claims.

The invention claimed is:

1. A method of adjusting an active noise cancelling (ANC) system in which a microphone is acoustically coupled to a loudspeaker via a secondary path and the loudspeaker is electrically coupled to the microphone via an ANC filter, the method comprising:

measuring phase characteristics of the secondary path in various modes of operation;

determining from the measured phase characteristics a statistical dispersion of the phase characteristics in the various modes of operation;

determining from the statistical dispersion a minimum phase margin and a maximum gain margin;

adjusting the ANC filter to exhibit in any one of the modes of operation phase characteristics that are equal to or greater than the minimum phase margin; and adjusting the ANC filter to exhibit in any one of the modes of operation amplitude characteristics that are equal to or smaller than the maximum gain margin.

2. The method of claim 1, in which the maximum gain margin is kept so small that the system is close to marginal stability or instability.

3. The method of claim 2, in which the maximum gain margin is equal to or smaller than at least one of 1 dB and 0.5 dB and 0.25 dB.

4. The method of claim 2, in which the system has a loop gain that is reduced by a value that is determined from the statistical dispersion.

5. The method of claim 1, in which at least one of the amplitude margin and the phase margin is frequency-independent.

6. The method of claim 1, in which the microphone may be arranged in the ear canal.

7. The method of claim 1, in which determining from the measured phase characteristics a statistical dispersion of the phase characteristics in the various modes of operation includes determining at least one of a worst case magnitude characteristic and a worst case phase characteristic.

8. The method of claim 7, in which the phase characteristic includes those phase values which are closest to the stability limits at 0° and 360° at each of a multiplicity of frequencies.

9. The method of claim 7, in which the phase margins are determined from the dispersion at the lower stability limit at 360°.

10. The method of claim 5, in which the phase margins are determined by multiplying each spread of distribution with a constant.

11. The method of claim 1, in which the gain margins are determined on the basis of the spread of distribution of the magnitude characteristic at each of a multiplicity of frequencies.

12. The method of claim 2, in which the maximum gain margin is smaller than 1 dB.

* * * * *